United States Patent
Steenwyk et al.

(10) Patent No.: US 11,452,630 B2
(45) Date of Patent: Sep. 27, 2022

(54) STENT DELIVERY SYSTEMS

(71) Applicant: BOSTON SCIENTIFIC SCIMED, INC., Maple Grove, MN (US)

(72) Inventors: Nicholas Scott Steenwyk, Sheboygan, WI (US); Brady Scott Logan, Maple Grove, MN (US); Rowan Olund Hettel, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 118 days.

(21) Appl. No.: 16/737,673

(22) Filed: Jan. 8, 2020

(65) Prior Publication Data
US 2020/0214866 A1 Jul. 9, 2020

Related U.S. Application Data

(60) Provisional application No. 62/790,336, filed on Jan. 9, 2019.

(51) Int. Cl.
*A61F 2/966* (2013.01)

(52) U.S. Cl.
CPC ...... *A61F 2/966* (2013.01); *A61F 2002/9665* (2013.01)

(58) Field of Classification Search
CPC .............. A61F 2/966; A61F 2002/9665; A61F 2230/0093; A61F 2/958; A61F 2002/9583; A61F 2002/9586; A61F 2002/9528; A61F 2002/9534; A61F 2002/9505; A61F 2002/9511; A61F 2/2427; A61F 2/2436; A61F 2/962; A61F 2/011; A61F 2/95
See application file for complete search history.

(56) References Cited

U.S. PATENT DOCUMENTS

| | | | |
|---|---|---|---|
| 5,980,533 A | 11/1999 | Holman | |
| 9,636,244 B2 | 5/2017 | Syed | |
| 2004/0097988 A1 | 5/2004 | Gittings et al. | |
| 2010/0100167 A1* | 4/2010 | Bortlein | A61F 2/95 623/1.11 |
| 2014/0200649 A1* | 7/2014 | Essinger | A61F 2/2439 623/1.12 |
| 2015/0265444 A1* | 9/2015 | Kitaoka | A61F 2/966 623/1.11 |
| 2018/0071125 A1* | 3/2018 | Bradway | A61F 2/966 |
| 2018/0116790 A1 | 5/2018 | Ratz et al. | |

FOREIGN PATENT DOCUMENTS

| | | |
|---|---|---|
| EP | 3292844 A1 | 3/2018 |
| WO | 2007022496 A2 | 2/2007 |
| WO | 2015157181 A1 | 10/2015 |

OTHER PUBLICATIONS

International Search Report and Written Opinion dated Apr. 8, 2020 for International Application No. PCT/US2020/012792, 19 pages.

* cited by examiner

*Primary Examiner* — Kelly J Bekker
*Assistant Examiner* — Andrew P. Restaino
(74) *Attorney, Agent, or Firm* — Seager, Tufte & Wickhem, LLP (57) ABSTRACT

Stent delivery systems including a deployment sheath for the stent, and an anti-catch member positionable adjacent to a proximal end of the deployment sheath and designed to allow the proximal end of the deployment sheath to be passed through the stent without catching on the stent.

20 Claims, 7 Drawing Sheets

STENT DELIVERY SYSTEMS

CROSS-REFERENCE TO RELATED APPLICATIONS

This application claims the benefit of priority under 35 U.S.C. § 119 to U.S. Provisional Application Ser. No. 62/790,336, filed Jan. 9, 2019, the entirety of which is incorporated herein by reference.

TECHNICAL FIELD

The present disclosure pertains to medical devices, and methods for manufacturing and using medical devices. More particularly, the present disclosure pertains to stents, stent delivery systems, and methods for manufacturing and using such devices and systems.

BACKGROUND

A wide variety of intracorporeal medical devices have been developed for medical use, for example, intravascular use, endoscopic use, and the like. Some of these devices include expandable stents, delivery devices and/or systems for expandable stents, and the like. These devices and/or systems are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for expandable stents and/or stent delivery systems.

An example stent delivery system includes: an inner member having a distal end region; a deployment sheath disposed along the distal end region of the inner member and defining a space between the inner member and the deployment sheath, the deployment sheath having a proximal end, the inner member and deployment sheath being designed to slide distally relative to a stent disposed in the space between the inner member and the deployment sheath in order to deploy the stent; and an intermediate member disposed along the inner member, the intermediate member including an anti-catch member, the intermediate member being movable relative to the deployment sheath such that the anti-catch member is positionable adjacent to the proximal end of the deployment sheath and designed to allow the proximal end of the deployment sheath to be passed through the stent without catching on the stent.

Alternatively or additionally to the embodiments above, wherein the anti-catch member includes a tapered outer surface.

Alternatively or additionally to any of the embodiments above, wherein the anti-catch member includes a collapsible member.

Alternatively or additionally to any of the embodiments above, wherein the anti-catch member includes a self-expanding member.

Alternatively or additionally to any of the embodiments above, wherein the anti-catch member includes a conically shaped tubular member.

Alternatively or additionally to any of the embodiments above, wherein the conically shaped tubular member includes a proximal portion coupled to the intermediate member, and an expandable distal portion.

Alternatively or additionally to any of the embodiments above, wherein the expandable distal portion includes a plurality of fingers.

Alternatively or additionally to any of the embodiments above, wherein the anti-catch member includes a distal portion having a first outer diameter, and a proximal portion having a second outer diameter, and the first outer diameter is greater than the second outer diameter.

Alternatively or additionally to any of the embodiments above, wherein the deployment sheath includes an inner diameter, and wherein the first outer diameter of the anti-catch member approaches the inner diameter of the deployment sheath.

Alternatively or additionally to any of the embodiments above, wherein the deployment sheath includes an inner surface, and the anti-catch member includes an outer surface that engages the inner surface of the deployment sheath.

Alternatively or additionally to any of the embodiments above, wherein the anti-catch member includes a tapered outer surface of a portion of the intermediate member.

Alternatively or additionally to any of the embodiments above, wherein the anti-catch member is movable relative to the deployment sheath such that it includes a first position in which the anti-catch member is spaced from the proximal end of the deployment sheath, and a second position in which the anti-catch member is positioned adjacent to the proximal end of the deployment sheath.

Alternatively or additionally to any of the embodiments above, wherein the anti-catch member is movable relative to the deployment sheath such that it includes a first position in which the anti-catch member is disposed within the deployment sheath distal of the proximal end of the deployment sheath, and a second position in which the anti-catch member is engaged with the deployment sheath at or adjacent the proximal end of the deployment sheath.

Alternatively or additionally to any of the embodiments above, wherein the anti-catch member includes a constrained configuration where the anti-catch member is disposed within the deployment sheath and an expanded configuration where at least a portion of the anti-catch member is disposed outside of the deployment sheath.

Alternatively or additionally to any of the embodiments above, wherein the anti-catch member includes an inner surface that is designed to engage an outer surface of the deployment sheath.

Alternatively or additionally to any of the embodiments above, further including a self-expanding stent disposed in the space between the inner member and the deployment sheath.

Alternatively or additionally to any of the embodiments above, where the anti-catch member is disposed in the space between the inner member and the deployment sheath.

An example stent delivery system includes: an inner member having a distal end region; a deployment sheath coupled to the inner member and disposed along the distal end region of the inner member, the deployment sheath having a proximal end; a stent disposed within a space between the inner member and the deployment sheath; an intermediate member disposed along the inner member and including an anti-catch member; the inner member and deployment sheath being designed to slide distally relative to the stent in order to deploy the stent; and the intermediate member including the anti-catch member being movable relative to the deployment sheath such that the anti-catch member includes a first position in which the anti-catch member is spaced from the proximal end of the deployment sheath and a second position in which the anti-catch member is positioned adjacent to the proximal end of the deployment sheath and is designed to allow the proximal end of the deployment sheath to be passed through the stent without catching on the stent.

Alternatively or additionally to any of the embodiments above, wherein when in the first position, the anti-catch member is disposed within the space between the inner member and the deployment sheath, and when in the second position, at least a portion of the anti-catch member is disposed outside of the deployment sheath.

An example method of deploying a stent includes: delivering a stent delivery system into the anatomy of a patient, the stent delivery system including; an inner member having a distal end region; a deployment sheath disposed along the distal end region of the inner member, the deployment sheath having a proximal end; a stent disposed within a space between the inner member and the deployment sheath; and an intermediate member disposed along the inner member and including an anti-catch member. The method includes deploying the stent by sliding the inner member and the deployment sheath distally relative to the stent; moving the anti-catch member relative to the deployment sheath such that the anti-catch member is positioned adjacent to the proximal end of the deployment sheath; and passing the deployment sheath through the stent, wherein the anti-catch member is designed to allow the proximal end of the deployment sheath to be passed through the stent without catching on the stent.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range (e.g. 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "axial", "circumferential", "longitudinal", "lateral", "radial", etc. and/or variants thereof generally refer to direction and/or orientation relative to a central longitudinal axis of the disclosed structure or device.

The terms "extent" and/or "maximum extent" may be understood to mean a greatest measurement of a stated or identified dimension, while the term "minimum extent" may be understood to mean a smallest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" or "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features or configurations. It is to be understood that the numerical nomenclature is not intended to be limiting and is exemplary only. In some embodiments, alterations of and deviations from previously-used numerical nomenclature may be made in the interest of brevity and clarity. That is, a feature or configuration identified as a "first" element or configuration may later be referred to as a "second" element or configuration, a "third" element or configuration, etc. or may be omitted entirely, and/or a different feature or configuration may be referred to as the "first" element or configuration. The meaning and/or designation in each instance will be apparent to the skilled practitioner.

Stents, and stent delivery systems are utilized throughout the world in medical procedures. Many such systems generally have an outer and/or delivery sheath that constrains the expandable stent in a radially contracted, delivery state. The self-expanding stent can be freed from the restraint of the delivery sheath by removing the sheath from the constrained stent, allowing the expandable stent to expand to a radially expanded, deployed state.

For example, some stent delivery system works by proximally retracting the deployment sheath relative to the stent and/or distally pushing the stent relative to the deployment sheath, causing the stent to begin deployment at its distal end. Once unconstrained by the deployment sheath, the stent can expand, for example, to force itself against the luminal wall of the body lumen. Such distal deployment systems (DDS) may be desirable, for example, where precise placement of the distal end of the stent is of particular concern.

In some other cases, the stent delivery system works by distally advancing the deployment sheath relative to the stent and/or proximally pushing the stent relative to the deployment sheath, causing the proximal end of the stent to deploy first. Such proximal deployment systems (PDS) may be desirable, for example, where precise placement of the proximal end of the stent is of particular concern.

One common characteristic of proximal deployment systems is that the delivery sheath extends distally beyond the distal end of the stent during and/or after deployment of the stent. As such, to remove the delivery system from the anatomy after deployment of the stent, the deployment sheath often needs to be withdrawn proximally back through the deployed stent.

During proximal withdrawal of the delivery sheath back through the deployed stent, there is a possibility that a portion of the stent, such as the distal end of the stent, may be snagged, caught, or disrupted by a portion of the delivery sheath, such as the proximal end of the delivery sheath. For example, the delivery sheath may have an open proximal end from which the stent was deployed, and this open proximal end may provide a step and/or edge and/or surface that may catch or snag on the stent when withdrawing the delivery sheath back through the deployed stent. Additionally and/or alternatively, the delivery sheath is typically moved and/or deployed using an inner member having a small diameter compared to that of the diameter of the deployment sheath. The difference and/or step up in diameter between the inner member and the open proximal end of the deployment sheath may provide an edge and/or surface and/or step that may catch or snag the stent when withdrawing the delivery sheath back through the deployed stent. Catching and/or snagging the stent during withdrawal of the deployment sheath can create problems. For example, catching and/or snagging the stent with the proximal end of the deployment sheath during withdrawal could cause difficulties in withdrawal, stent migration, stent or delivery system damage, vessel damage, and/or embolism risk if a part of the delivery system and/or stent breaks. The risk of catching and/or snagging may be exacerbated if the stent is located along a curve.

Accordingly, there is an ongoing need for improvements in catheters, devices, and/or systems that deliver self-expanding stents, to help reduce and/or prevent catching and/or snagging of the stent during withdrawal of the delivery sheath and/or other components of the delivery system. As such, some embodiments of the present disclosure may include methods, devices, and/or systems that may be configured or designed to help reduce and/or prevent such catching and/or snagging. For example, it may be desirable to provide a stent delivery device and/or system that includes an anti-catch member that is positionable adjacent to the proximal end of the deployment sheath and/or other portions of the delivery system, and is designed to allow portions of the delivery system, such as the proximal end of the deployment sheath, to be passed through the stent while reducing or eliminating the risk of catching or snagging on the stent.

FIGS. 1-5 show an example embodiment of a stent delivery system 10 disposed within a body lumen, such as within a blood vessel 8. The stent delivery system 10 includes an inner member 14 including a distal end region 16, and a deployment sheath 20 disposed along the distal end region 16. The deployment sheath 20 may be coupled to the inner member 14, for example, at the distal end 24. A space 19 is defined between the inner member 14 and the deployment sheath 20. An intermediate member 40 including an anti-catch member 50 is movably and/or slidably disposed along the inner member 14 and/or along the deployment sheath 20. A stent 30, for delivery, may be disposed in the space 19. This stent delivery system 10 is designed to work by distally advancing/translating the deployment sheath 20 relative to the stent 30 and/or proximally pushing/translating the stent 30 relative to the deployment sheath 20, causing the proximal end of the stent to deploy first. As such, this stent delivery system 10 is a configured to be a proximal deployment systems (PDS).

Figure 1:
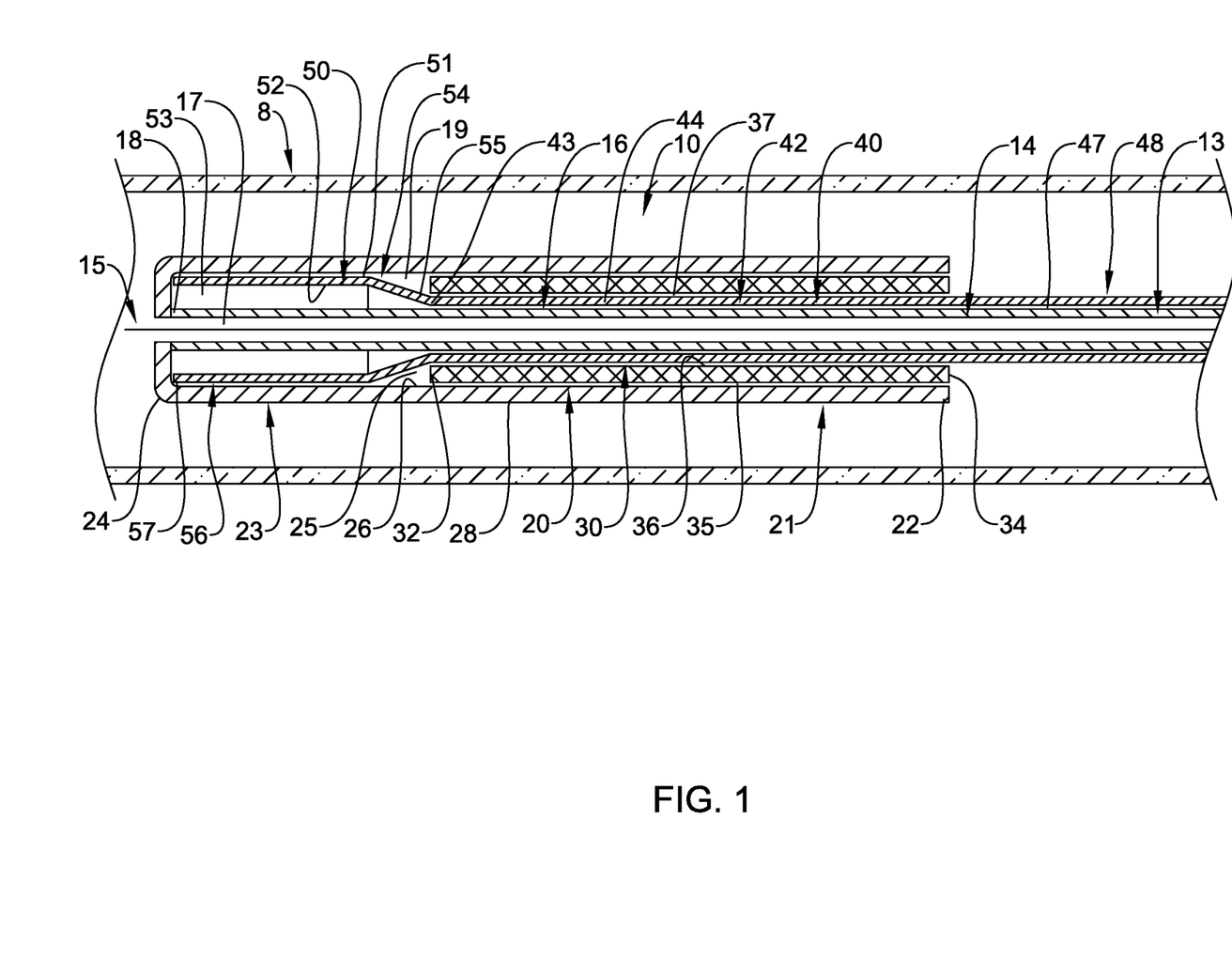
FIG. 1 is cross sectional side view of a portion of an example embodiment of a stent delivery system disposed within a vessel in a first configuration prior to deployment of the stent.

The stent delivery system 10 may include one or more configurations during use, for example: one or more delivery configuration(s), for delivering a stent 30 to a treatment location; one or more deployment configuration(s) for deploying the stent 30 at the desired treatment location; and one or more withdrawal configuration(s) for removal the delivery system 10 after deployment of the stent 30. FIGS. 1-5 in progression show the stent delivery system 10 in various configurations as it is used to deliver and deploy the stent 30, and then position the anti-catch member 50 adjacent the proximal end of the deployment sheath 20 for withdraw the stent deployment system 10. For example, FIG. 1 shows the stent delivery system 10 in a delivery configuration. FIGS. 2-5 shows the stent delivery system 10 in various other configurations, including deployment configuration(s) at various stages of stent deployment and positioning of the anti-catch member 50 (e.g. FIGS. 2-4), and withdrawal configuration(s) (e.g. FIG. 5).

In some embodiments, the inner member 14 may be and/or included a solid shaft, a tubular member or shaft, such as a hypotube, catheter, etc., and/or combinations thereof. In some instances, the inner member 14 may include a guidewire lumen 17 for advancing the stent delivery system 10 over a guidewire 15 to a treatment location. The inner member 14 includes a distal end region 16, a distal end 18, and a proximal region 13 that will include a proximal end. The inner member 14 may be coupled to the deployment sheath 20 for movement therewith. For example, a distal end 18 of the inner member 14 may be coupled to the distal end 24 of the deployment sheath 20, but other configurations are contemplated. The inner member 14 may be adapted, sized, designed and/or configured to be used to manipulate and/or move the deployment sheath 20 relative to other components of the system 10, for example, relative to the stent 30 and/or intermediate member 40 and/or the anti-catch member 50. In some embodiments, a proximal end of the inner member 14 may include an enlarged flange, a hub, a handle, and/or other suitable means for handling and/or manipulating the inner member 14 (and therefore the deployment sheath 30) relative to the stent 30 and/or the intermediate member 40 or other portions of the device 10. In at least some embodiments, the inner member 14 may be positioned coaxially within the intermediate member 40 and/or the stent 30 and/or the deployment sheath 30 and/or other portions of the device 10. Some suitable but non-limiting materials for the inner member 14 are, for example, metallic materials, polymer materials, composite materials, synthetic materials, etc., are described below.

In some embodiments, the deployment sheath 20 may be and/or includes a tubular structure or member. The deployment sheath 20 includes a wall having an outer surface 28 and an inner surface 26 defining the lumen 25. The deployment sheath 20 may be disposed along the distal end region 16 of the inner member 14. The deployment sheath 20 may be coupled to the inner member 14 for movement therewith, and to define the stent space 19 there between. In the embodiment shown, a distal end 24 of the deployment sheath 20 is coupled to the distal end 18 of the inner member 14, but other attachment configurations are contemplated. The deployment sheath 20 may be a separate component affixed or attached to the inner member 14 using a suitable attachment technique, or may be part of and/or of monolithic or unitary construction with the inner member 14 (e.g. a singular part or component). The deployment sheath 20 and/or the lumen 25 of the deployment sheath 20 may be sized and/or configured to house the stent 30 in a radially collapsed or constrained configuration (e.g. within the space 19). For example, the deployment sheath 20 may surround the expandable stent 30 to retain the stent 30 in a radially constrained state during delivery of the stent 30 to a target site in a body lumen. The deployment sheath 20 and/or the lumen 25 of the deployment sheath 20 may also be sized and/or configured to house a distal region 42 of the intermediate member 40 and/or the anti-catch member 50 (e.g. within the space 19), as discussed and shown herein. In some embodiments, the deployment sheath 20 may be sized and configured for passage through an introducer, a delivery catheter, a guide catheter, an endoscope, and/or other medical device, for example, during delivery. Some suitable but non-limiting materials for the deployment sheath 20 include, for example, metallic materials, polymer materials, composite materials, synthetic materials, etc., as are described below.

The stent 30, for delivery by the stent delivery system 10, may be a self-expanding stent, and may be configured to shift between a radially collapsed configuration when radially constrained and a radially expanded configuration when radially unconstrained. In some embodiments, the stent 30 may be biased toward the radially expanded configuration in an equilibrium state. In some embodiments, the stent 30 may be self-biased toward the radially expanded configuration. The stent 30 may include a distal end 32, a proximal end 34, an outer surface 35, and an inner surface 36 defining a stent lumen 37. As shown in FIG. 1, the stent 30 may be disposed within the deployment sheath 20 (e.g. within the lumen 25 and/or space 19) to retain the stent 30 in a radially constrained state during delivery of the stent 30 to a target site in a body lumen 8.

In some embodiments, the stent 30 may be formed by cutting or removing material from a unitary tubular member, such as by laser cutting or other suitable processes. In some embodiments, the stent 30 may be formed as a braided, woven, and/or knit stent from one or more wires, filaments, etc. The stent 30 may have an overall length suitable for the intended procedure and/or use. For example, the stent 30 may have an overall length ranging from less than 5 mm to more than 200 mm. In some embodiments, the stent 30 may be formed to an overall diameter or outer extent ranging from 1 mm to 30 mm, depending on the intended usage. Some suitable but non-limiting materials for the stent 30 include, for example, metallic materials, polymer materials, composite materials, synthetic materials, etc., are described below.

In some embodiments, the intermediate member 40 may be and/or includes a tubular member or shaft, such as a hypotube, catheter, etc., and/or combinations thereof. The intermediate member 40 may include a tubular structure including a wall having an outer surface, and an inner surface defining a lumen 47. The intermediate member 40 may include the distal region 42 including a distal end 43, and a proximal region 48 that will include a proximal end. In some embodiments, a proximal end of the intermediate member 40 may include an enlarged flange, a hub, a handle, and/or other suitable means for handling and/or manipulating the intermediate member 40 (and therefore the anti-catch member 50 as described herein) relative to the inner member 14 and/or the deployment sheath 20 and/or the stent 30 and/or other portions of the device 10. In at least some embodiments, the intermediate member 40 may be positioned coaxially over the inner member 14, such that a portion of the inner member 14 extends within the lumen 47. The distal region 42 of the intermediate member 40 may also be sized and/or configured to extend within and/or be housed within the deployment sheath 20 and/or the lumen 25 of the deployment sheath 20, as discussed and shown herein. When so positioned, the distal region 42 of the intermediate member 40 may coaxial with the deployment sheath 20.

The intermediate member 40 may be adapted, sized, designed and/or configured to be used to manipulate and/or move the anti-catch member 50 and/or stent 30 relative to other components of the system 10, for example, relative to the deployment sheath 20 and/or inner member 14, as is described herein. Additionally and/or alternatively, the intermediate member 40 may be adapted, sized, designed and/or configured to function as a stent bed and/or stent rest. For example, in some configurations (such as a delivery configuration and/or a deployment configuration) the distal region 42 of the intermediate member 40 may be disposed within the deployment sheath 20, and the stent 30, in a compressed state within the deployment sheath 20, may be disposed around (e.g. surround) a portion of the distal region 42 of the intermediate member 40. The distal region 42 of the intermediate member 40 may extend longitudinally within the stent lumen 37, and may be coaxial with the stent 30. In some embodiments, the stent 30 may be compressed into engagement with the outer surface of the distal region 42 of the intermediate member 40. In other embodiments, the stent 30 may be disposed about the distal region 42 of the intermediate member 40, but not necessarily compressed into engagement with the outer surface thereof. Some suitable but non-limiting materials for the intermediate member 40 are, for example, metallic materials, polymer materials, composite materials, synthetic materials, etc., as are described below.

The intermediate member 40 includes the anti-catch member 50. The anti-catch member 50 may be disposed on and/or along the distal end region 42 of the intermediate member 40, and may be coupled to the intermediate member 40 for movement therewith. The anti-catch member 50 may include a proximal region 54, a proximal end 55, a distal region 56, and a distal end 57. The anti-catch member 50 may include an outer surface 51, and an inner surface 52 defining lumen 53 (which may be in communication with and/or common with the lumen 47 of the intermediate member 40).

The anti-catch member 50 may be a separate component affixed or attached to the intermediate member 40 using a suitable attachment technique, or may be part of and/or of monolithic or unitary construction with the intermediate member 40 (e.g. a singular part or component). For example, the anti-catch member 50 may be a separate tubular component that is bonded, welded, glued, soldered, heat shrunk or otherwise attached to the intermediate member 40. In other examples, the anti-catch member 50 may be an integral extension, portion, or part of the intermediate member 40 that includes a widened and/or increased diameter and/or tapered outer surface. In the embodiment shown in FIGS. 1-5, the anti-catch member 50 is coupled to the distal end 43 of the intermediate member 40, and extends distally beyond the distal end 43 of the intermediate member 40, but other configurations are contemplated. For example, in other embodiments, the anti-catch member 50 may be disposed on and/or along the distal region 42 of the intermediate member 40 such that it is spaced from (e.g. is proximal from) and/or overlaps the distal end 43 of the intermediate member 40. Some suitable but non-limiting materials for the anti-catch member 50 are, for example, metallic materials, polymer materials, composite materials, synthetic materials, etc., as are described below.

The anti-catch member 50 is a feature and/or structure on the distal region 42 of the intermediate member that may be positioned and/or is positionable adjacent to a proximal end 23 of the deployment sheath 20 after deployment of the stent 30. The anti-catch member 50 may include structure that, when positioned adjacent to the proximal end 22 of the deployment sheath 20, is adapted, sized, designed and/or configured to help create a transition adjacent to the proximal end 22 of the deployment sheath 20 that allows the deployment sheath 20 to be passed proximally back through the deployed stent 30 while reducing or eliminating the risk of the proximal end 22 of the deployment sheath 20 catching or snagging on the stent 20. The anti-catch member 50 may include one or more of a number of structural features that may aid in this function.

For example, the anti-catch 50 may include widened diameter structure (e.g. widened diameter relative to the distal region of the intermediate member 42 and/or distal region of the inner member 14) designed to reduce, close, guard, cover, fill, and/or protect all or a portion of the open proximal end of the deployment sheath 20. Additionally and/or alternatively, the anti-catch member 50 may include structure to provide a tapered transition adjacent the open proximal end of the deployment sheath 20. For example, the anti-catch member 50 may provide for a tapered transition from the open proximal end 22 of the deployment sheath 20 to the outer surface of the distal region 42 of the intermediate member 40. The widened diameter and/or tapered structure of the anti-catch member 50 (e.g. relative to the distal region of the intermediate member 42), when appropriately positioned adjacent to the proximal end 22 of the deployment sheath 20, may help reduce and/or cover and/or hide and/or eliminating a step and/or a gap and/or an edge and/or a surface on or adjacent the proximal end 22 of the deployment sheath 20 that may catch or snag on the stent 30 when withdrawing the delivery sheath 20 proximally back through the deployed stent 30. The anti-catch member 50 may generally include at least a portion thereof that has a diameter that is wider than a diameter of the distal region 42 of the intermediate member 40. Additionally, or alternatively, the anti-catch member 50 may generally include a tapered outer surface. In some embodiments, the anti-catch member 50 may include a widened generally conical and/or cylindrical portion having a tapered outer surface, and having an outer extent or diameter along at least a portion thereof that is greater than the outer extent or diameter of the distal region 42 of the intermediate member 40 and/or greater than the outer extent or diameter of the distal region 16 of the inner member 14.

Additionally and/or alternatively, the anti-catch member 50 may be adapted, sized, designed and/or configured to function as a distal bumper and/or distal stop for the stent 30. For example, the anti-catch member 50 may include a widened portion that is designed to engage the distal end of the stent 30 when the stent is in a constrained configuration within the deployment sheath 30, and prevent distal movement of the stent 30 relative to and/or with the deployment sheath 20 during distal translation of the deployment sheath 20 in the course of stent deployment. Additionally and/or alternatively, anti-catch member 50 may be used as a stop or bumper, in combination with the intermediate member 40, to move the stent 30 proximally out of the deployment sheath 20 in the course of stent deployment.

In some embodiments, all or portions of the anti-catch member 50 may be configured to shift between a radially collapsed configuration when radially constrained and a radially expanded configuration when radially unconstrained. The anti-catch member 50, or portions thereof, may be self-expanding. In some embodiments, all or portions of the anti-catch member 50 may be biased toward the radially expanded configuration in an equilibrium state. In some embodiments, anti-catch member 50, or portions thereof, may be self-biased toward the radially expanded configuration. In yet other embodiments, the anti-catch member 50 is not and/or does not include a collapsible/expandable portion or component (some embodiments of which are discussed further herein).

Figure 2:
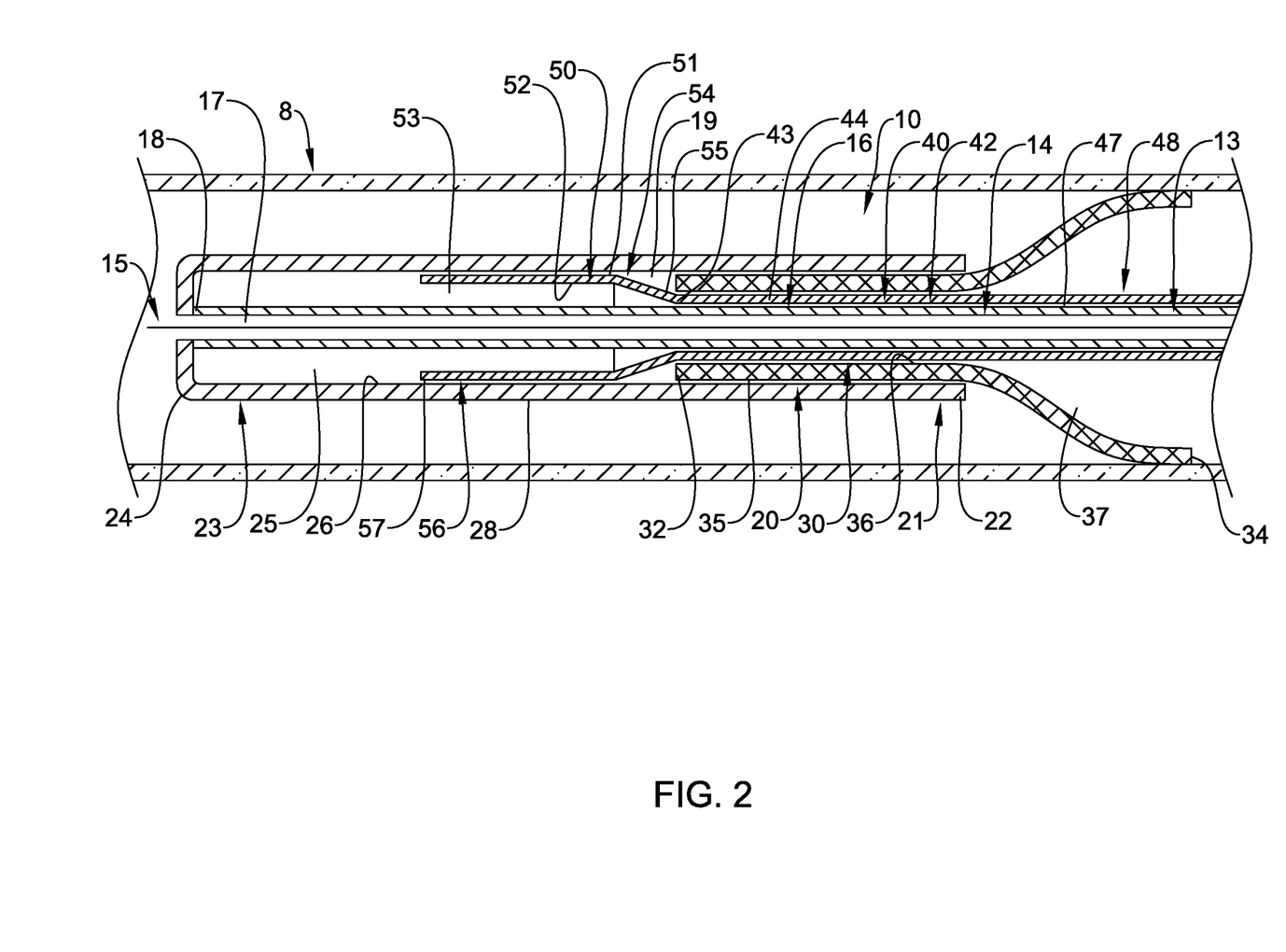
FIG. 2 is cross sectional side view of the example embodiment of FIG. 1 shown in another configuration during deployment of the stent wherein the stent is partially deployed, and wherein an anti-catch member is positioned within a deployment sheath spaced from and/or distal to the proximal end of the deployment sheath.
Figure 3:
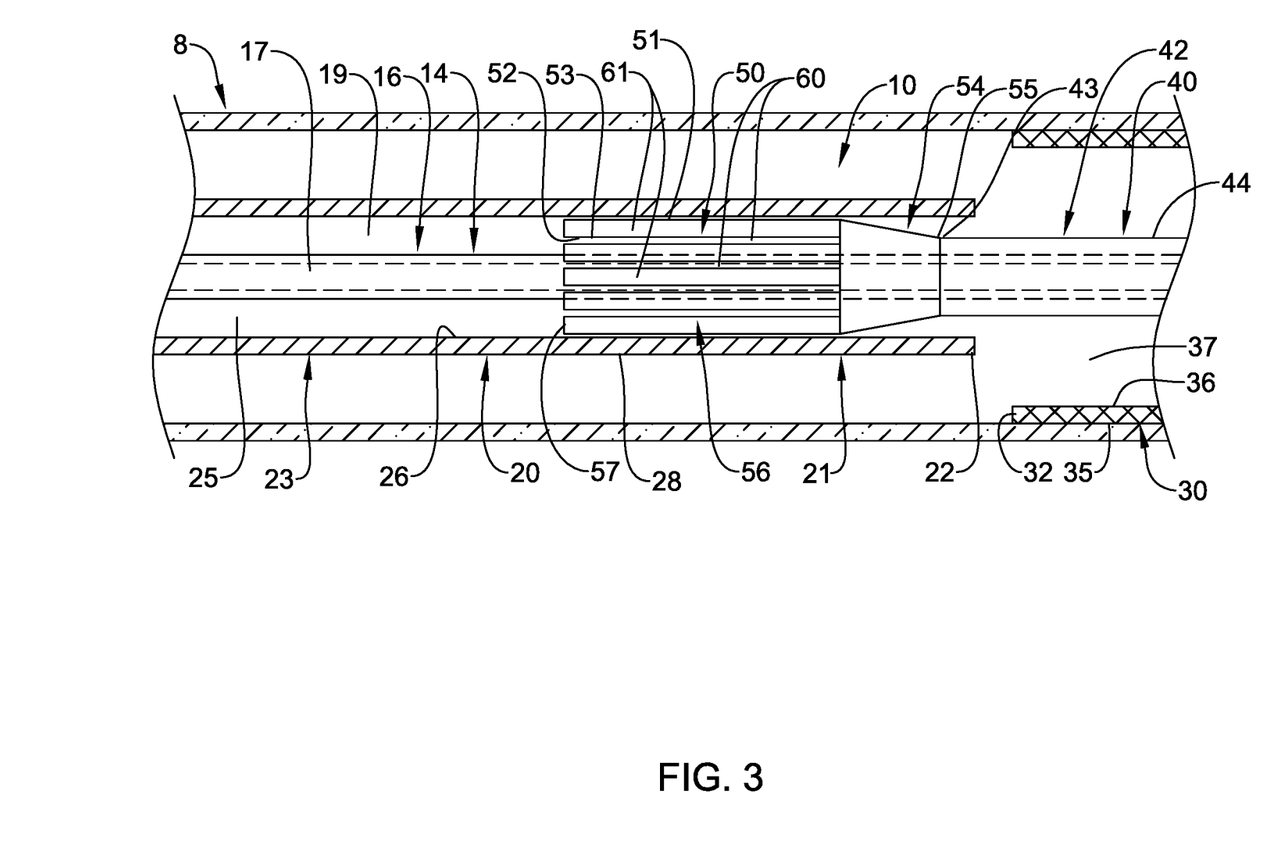
FIG. 3 is partial cross sectional side view of the example embodiment of FIG. 2 shown in another configuration after deployment of the stent, and the anti-catch member is positioned within a deployment sheath spaced from and/or distal to the proximal end of the deployment sheath, wherein the vessel, stent, and deployment sheath are shown in cross-section side views, while an inner member and an intermediate member including the anti-catch member, are shown in non-cross-sectional side views.
Figure 4:
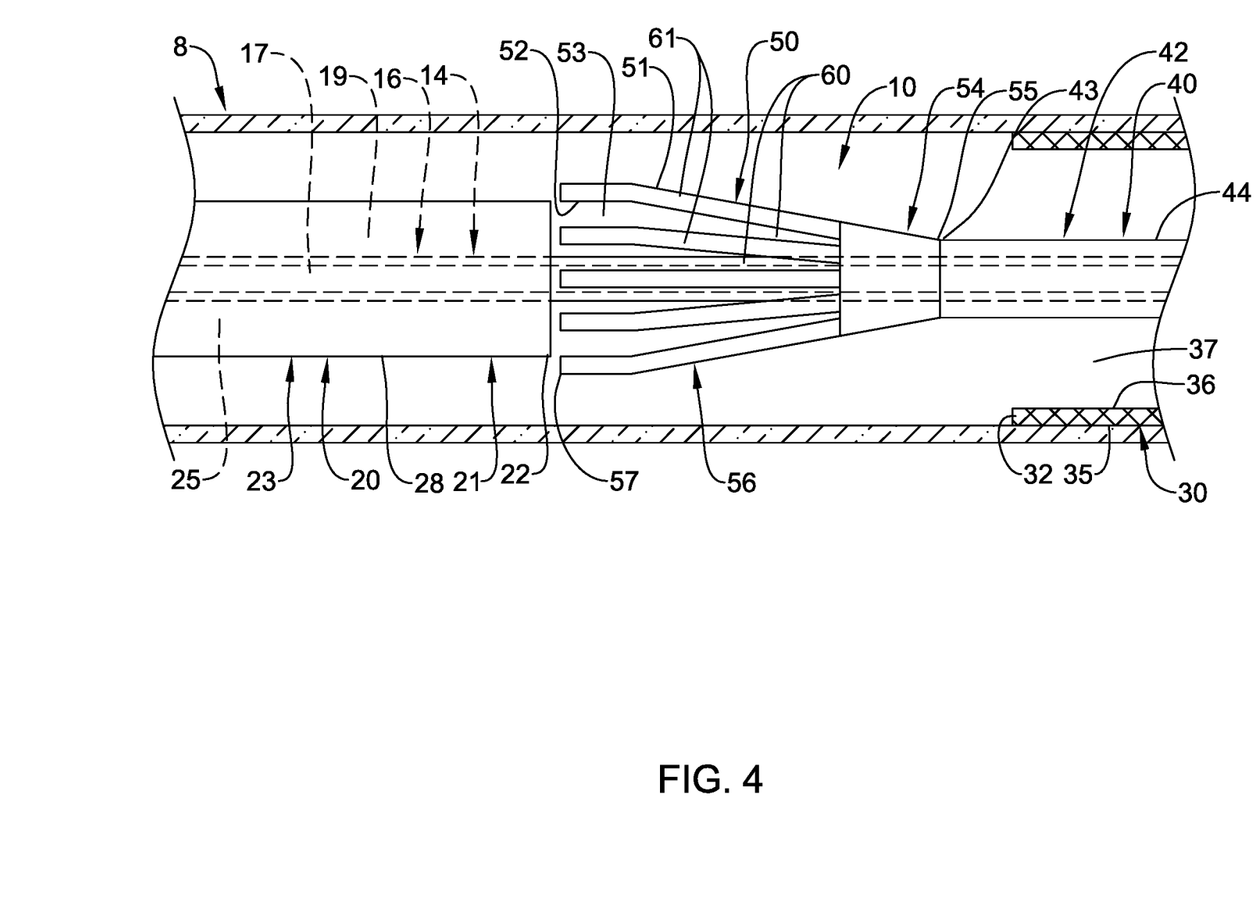
FIG. 4 is partial cross sectional side view of the example embodiment of FIG. 3, shown in another configuration after deployment of the stent, where the intermediate member and anti-catch member are moved proximally relative to the deployment sheath, and the anti-catch member is in an expanded state, showing the vessel and stent in cross-sectional side view, and the delivery system in non-cross sectional side view.
Figure 5:
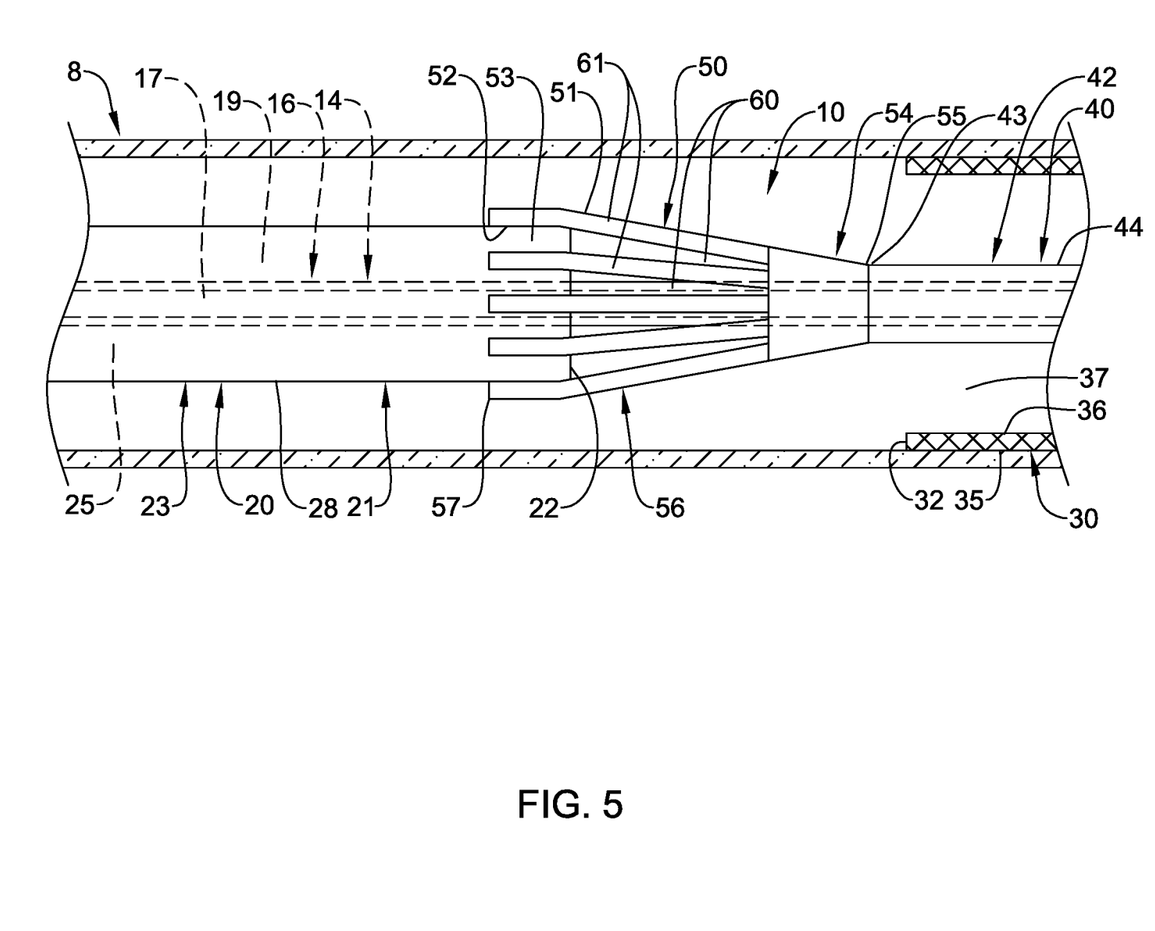
FIG. 5 is partial cross sectional side view of the example embodiment of FIG. 4, shown in another configuration with the intermediate member and anti-catch member moved distally relative to the deployment sheath such that the anti-catch member is positioned adjacent to the proximal end of the deployment sheath.

In the embodiment shown in FIGS. 1-5, at least the distal region 56 of the anti-catch member 50 may be configured to shift between a radially collapsed configuration when radially constrained by the delivery sheath 20 (e.g. as shown in FIGS. 1-3) and a radially expanded configuration when radially unconstrained by the delivery sheath 20 (as shown in FIGS. 4-5). In the configurations shown in FIGS. 1-3, anti-catch member 50 may be disposed within the deployment sheath 20 (e.g. within the lumen 25 and/or space 19) to retain at least the distal region 56 of the anti-catch member 50 in a radially constrained state (e.g. during delivery and/or stent deployment configurations). In the configurations shown in FIGS. 4 and 5, the anti-catch member 50 may be disposed outside of the deployment sheath 20 (e.g. withdrawn proximally from the lumen 25 and/or space 19) and at least the distal region 56 is shifted to a radially expanded configuration when radially unconstrained by the delivery sheath 20. The anti-catch member 50 may be a cone and/or conically shaped tubular member including a proximal portion coupled to the intermediate member 40, and an expandable distal region 56.

In some embodiments, at least a portion of the anti-catch member 50 includes a tapered outer surface 51. For example, at least a portion of the anti-catch member 50 tapers from a smaller outer diameter to a larger outer diameter as it extends distally. Over at least a region of the length of the anti-catch member 50, an outer extent or diameter at a more distal portion of anti-catch member 50 is greater than an outer extent or diameter of the anti-catch member 50 at a more proximal portion thereof, and the transition between these different diameters may be tapered. The taper may occur at a constant angle relative to the longitudinal axis, or may occur in a curvilinear fashion. In yet other embodiments, the taper may occur in a stepwise fashion, for example, at varying angles along the length thereof and/or including a series of tapered and non-tapered sections. If the anti-catch member 50 is configured to shift between a radially collapsed configuration and a radially expanded configuration, the one or more tapers in the outer surface 51 of the anti-catch member 50 may exist in the expanded configuration, in the contracted configuration, or both.

For example, in FIGS. 1-3, the anti-catch member 50 is shown in a radially collapsed configuration, where the proximal region 54 includes a portion having a tapered outer surface (which increases in outer diameter as it extends distally), but the distal region 56 does not show a tapered outer surface, for example, due to being constrained within the deployment sheath 20. However, as shown in FIGS. 4 and 5, once unconstrained by the deployment sheath 20, the distal region 56 may expand and may then also include one or more portion having a tapered outer surface (which increases in outer diameter as it extends distally).

In some embodiments, the anti-catch member 50 may be a tubular and/or conical member having a generally solid wall made of a suitable material. In other embodiments, the anti-catch member 50 may be formed as a coiled, braided, woven, and/or knitted feature made from one or more wires, windings, filaments, etc. Additionally, and/or alternatively, the anti-catch member 50 may be a tubular member that may include one or more slits 60 formed therein, for example, as show in FIGS. 3-5. The slits may provide for a greater degree of expandability and/or flexibility. If a plurality of slits 60 are present, a plurality of distally extending fingers 61 may be formed in and/or be included in the anti-catch member, such as in the distal region 56. The plurality of fingers 61 may make up the distal region 56 of the anti-catch member, may be expandable, and may include and/or make up at least a portion of the tapered outer surface of the anti-catch member 50.

The anti-catch member 50 may include the open distal end 57. For example, the anti-catch ember may be and/or include a tubular and/or conical and/or cup shaped member (with or without the slits 60 and/or the fingers 61) having an opening into the lumen 53 at the distal end 57 thereof. In some embodiments, the anti-catch member 50 may include the distal region 56 adapted, configured and/or sized to engage the deployment sheath 20, for example, engage the proximal end 22 and/or distal region 21 of the deployment sheath 20 when positioned adjacent thereto. For example, in some embodiments, the open distal end 57 may be designed and/or configured to accept and/or receive and/or engage the proximal end 22 of the deployment sheath 20. For example, as shown in FIG. 5, when the anti-catch member 50 is expanded, the opening in the distal end 57 may be sized and configured to accept the proximal end 22 of the deployment sheath (see, e.g. FIG. 5). In some embodiments, the inner surface 52 of the anti-catch member 50 may engage the outer surface 28 of the deployment sheath 20 at and/or adjacent the proximal end 22 of the deployment sheath. In some embodiments, the inner surface 52 of the anti-catch member 50 and/or fingers 61 may include and/or have applied thereto a lubricious and/or anti-stick and/or low friction surface and/or coating and/or material. Such a surface or coating may allow for easier engagement and/or disengagement of the anti-catch member 50 with the deployment sheath 20.

As seen in FIG. 5, when positioned adjacent to the proximal end 22 of the deployment sheath 20, the anti-catch member 50 may function to guard, cover, close, fill, reduce and/or protect all or a portion of the open proximal end 22 of the deployment sheath 20 and provide a tapered transition adjacent the open proximal end 22 of the deployment sheath 20, for example, to an outer surface 44 of the intermediate member 40. This may help to facilitate smooth removal/proximal withdrawal, and prevent and/or reduce likelihood that the proximal end 22 of the deployment sheath 20 will catch or snag on the stent during removal/proximal withdrawal thereof.

In some embodiments, the anti-catch member 50 may engage the proximal end 22 of the deployment sheath 20 in an end to end and/or abutting relationship when disposed adjacent the proximal end 22. For example, the distal end 57 and/or the distal region 56 of the anti-catch member 50 may include and/or expand to a diameter that may be sized and/or configured to abut and/or to be positioned and/or positional into an abutting relationship with the proximal end 22 of the deployment sheath 20. When positioned adjacent to the proximal end 22 of the deployment sheath 20 in an abutting relationship (e.g. proximal end 22 to distal end 57, the anti-catch member 50 may function to guard, cover, close, fill, reduce and/or protect all or a portion of the open proximal end 22 of the deployment sheath 20 and provide a tapered transition adjacent the open proximal end 22 of the deployment sheath 20, for example, to the outer surface 44 of the intermediate member 40. This may help to facilitate smooth removal/proximal withdrawal, and prevent and/or reduce likelihood that the proximal end 22 of the deployment sheath 20 will catch or snag on the stent during removal/proximal withdrawal thereof.

In some embodiments, the anti-catch member 50 may engage the inner surface 26 of the deployment sheath 20. For example, the deployment sheath 20 includes a lumen 25 having an inner diameter and defining an inner surface 26. The anti-catch member 50 may include a portion thereof (e.g. distal portion 56) having an outer diameter, and the outer diameter of the portion of the anti-catch member may approach and/or be about the same as the inner diameter of the deployment sheath 20 when the anti-catch member 50 is disposed therein. As such, there may be some frictional engagement between the inner surface 26 of the deployment sheath 20 and the outer surface 51 of the anti-catch member.

As indicated herein, the stent delivery system 10 is designed to work to deploy the stent 30 by distally advancing/translating the deployment sheath 20 relative to the stent 30 and/or proximally pushing/translating the stent 30 relative to the deployment sheath 20, causing the proximal end 34 of the stent 30 to deploy first. As such, the inner member 14 and deployment sheath 20 may be axially, longitudinally, slidably, and/or rotatably moved and/or translated together relative to the stent 30 and/or relative to the intermediate member 40, including the anti-catch member 50. Such movement will be used to deploy the stent 30, and also be used to move the anti-catch member 50 from a position in which the anti-catch member 50 is spaced from the proximal end 22 of the deployment sheath 20 to a position where the anti-catch member 50 is positioned adjacent the proximal end 22 of the deployment sheath 20. A progressive review and discussion of FIGS. 1-5 can be useful to illustrate the use of the stent deployment system 10 to deliver and deploy the stent 30, position the anti-catch member 50 adjacent the proximal end of the deployment sheath, and withdraw the stent deployment system 10.

FIG. 1 shows the stent deployment system 10 in a delivery configuration, with the stent 30 in a compressed state fully within the deployment sheath 20 (e.g. within the lumen 25 and/or space 19), and disposed around the distal region 42 of the intermediate member 40. The anti-catch member 50 is disposed distally of the stent 30 within the deployment sheath 20. As can be appreciate, in this configuration, the anti-catch member 50 is in a position spaced from and/or distal of the proximal end 22 of the deployment sheath 20. In this configuration, the stent deployment system 10, including the stent 30, may be delivered to a treatment location, for example, within the blood vessel 8.

FIG. 2 shows the stent deployment system 10 in another and/or deployment configuration, wherein the sent 30 is partially deployed. In particular, FIG. 2 shows relative distal translation of the inner member 14 and the deployment sheath 20 relative to the stent 30 and the intermediate member 40 (including the anti-catch member 50). Or stated differently, FIG. 2 shows relative proximal translation of the stent 30 and intermediate member 40 (including the anti-catch member 50) relative to the inner member 14 and the deployment sheath 20. A proximal portion of the stent 30 may exert a radially outward force and expand once the deployment sheath 20 is removed therefrom, thereby permitting the proximal portion of the stent 30 to expand toward the expanded configuration. As the proximal portion of the stent 30 radially expands, a distal portion of the stent 30 may be retained in the radially collapsed configuration within the deployment sheath 20. For example, the distal portion of the stent 30 is retained in the collapsed configuration by the deployment sheath 20. As such, the stent 30 is partially compressed (distal portion within the deployment sheath 20) and partially expanded (proximal portion outside of the deployment sheath 20). The stent 30 is still disposed around (e.g. surrounds) the distal region 42 of the intermediate member 40, and the anti-catch member 50 is disposed distally of the stent 30 within the deployment sheath 20. In this configuration, the anti-catch member 50 has moved proximally within the deployment sheath 20, but is also still disposed within the deployment sheath 20 in a position spaced from and/or distal of the proximal end 22 of the deployment sheath 20. During this translational movement, the anti-catch member 50 may act as a distal stop and/or bumper for the stent 30, preventing distal movement of the stent relative to and/or with the deployment sheath 20.

FIG. 3 shows the stent deployment system 10 in another and/or deployment configuration, wherein the sent 30 is fully deployed. In particular, FIG. 3 shows additional relative distal translation of the inner member 14 and the deployment sheath 20 relative to the stent 30 and the intermediate member 40 (including the anti-catch member 50). Or stated differently, FIG. 3 shows additional relative proximal translation of the stent 30 and intermediate member 40 (including the anti-catch member 50) relative to the inner member 14 and the deployment sheath 20. This additional relative translation of the components may release the intermediate and distal portions of the stent 30, progressively, from the deployment sheath 20, until the stent 30 is fully deployed, as shown. During this translational movement, the anti-catch member 50 may again act as a distal stop and/or bumper for the stent 30, preventing distal movement of the stent 30 relative to and/or with the deployment sheath 20. The stent 30 exerts a radially outward force and expands once the deployment sheath 20 is removed therefrom. As such, the stent 30 is in a fully expanded configuration, and is deployed within the vessel. The distal region 42 of the intermediate member 40 is still disposed within the lumen of the stent 30. The deployment sheath 20 and the distal region of the 16 of the intermediate member 14 are disposed distally of the deployed stent 30. The anti-catch member 50 is disposed within the deployment sheath 20 (distal of the stent 30). In this configuration, the anti-catch member 50 has moved proximally within the deployment sheath 20 to a position which is closer to the proximal end 22, but is still in a position spaced from and/or distal of the proximal end 22.

FIG. 4 shows the stent deployment system 10 in another and/or transitional configuration, wherein the sent 30 is fully deployed, and the anti-catch member 50 has been moved to a position proximal of the deployment sheath 20. In particular, FIG. 4 shows additional relative distal translation of the inner member 14 and the deployment sheath 20 relative to the intermediate member 40, including the anti-catch member 50. Or stated differently, FIG. 4 shows additional relative proximal translation of the intermediate member 40, including the anti-catch member 50, relative to the inner member 14 and the deployment sheath 20. This additional translation of the components may move and/or release the anti-catch member 50 from within the deployment sheath 20. In this embodiment, the anti-catch member 50 is radially collapsible/expandable, and as such, exerts a radially outward force and expands once the deployment sheath 20 is removed therefrom. As such, the anti-catch member 50 is in an expanded configuration. The distal region 42 of the intermediate member 40 is still disposed within the lumen of the deployed stent 30, and the deployment sheath 20 and the distal region of the 16 of the intermediate member 14 are disposed distally of the deployed stent 30. The anti-catch member 50 is disposed proximal of the deployment sheath 20 and is spaced from (e.g. spaced proximally from) the proximal end 22 of the deployment sheath 20.

FIG. 5 shows the stent deployment system 10 in another and/or withdrawal configuration, wherein the sent 30 is fully deployed, and the anti-catch member 50 has been moved to a position adjacent the proximal end 22 of the deployment sheath 20. In particular, FIG. 5 shows relative distal translation of the intermediate member 40, including the anti-catch member 50, relative to the inner member 14 and the deployment sheath 20. Or stated differently, FIG. 5 shows relative proximal translation of the inner member 14 and the deployment sheath 20 relative to the intermediate member 40, including the anti-catch member 50. This translation of the components may move the anti-catch member 50 to a position adjacent the proximal end 22 of the deployment sheath 20. In this embodiment, the anti-catch member 50 is an expandable member that may engage the proximal end 22 of the deployment sheath 20. The distal region 42 of the intermediate member 40 is still disposed within the lumen of the deployed stent 30. The deployment sheath 20 and the distal region of the 16 of the intermediate member 14 are still disposed distally of the deployed stent 30. To withdraw the delivery system 10 from the anatomy, the deployment sheath 20 needs to be withdrawn proximally back through the deployed stent 30. The anti-catch member 50, when positioned adjacent to the proximal end 22 of the deployment sheath 20, may function to guard, cover, close, fill, reduce and/or protect all or a portion of the open proximal end 22 of the deployment sheath 20 and provide a tapered transition adjacent the open proximal end 22 of the deployment sheath 20 during withdrawal. As such, the deployment sheath 20 may be passed through the stent 30, and the anti-catch member is designed to allow the proximal end 22 of the deployment sheath 20 to be passed through the stent 30 without catching on the stent.

As can be appreciate, any of the configurations of the stent deployment system 10 where the anti-catch member 50 is spaced from the proximal end 22 of the deployment sheath 20 may be considered a first position, and any of the configurations of the stent deployment system 10 where the anti-catch member is adjacent the proximal end 22 of the deployment sheath 20 may be considered a second position, and that the anti-catch member is movable relative to the deployment sheath 20 such that it can be transitioned from a first position to a second position.

Figure 6:
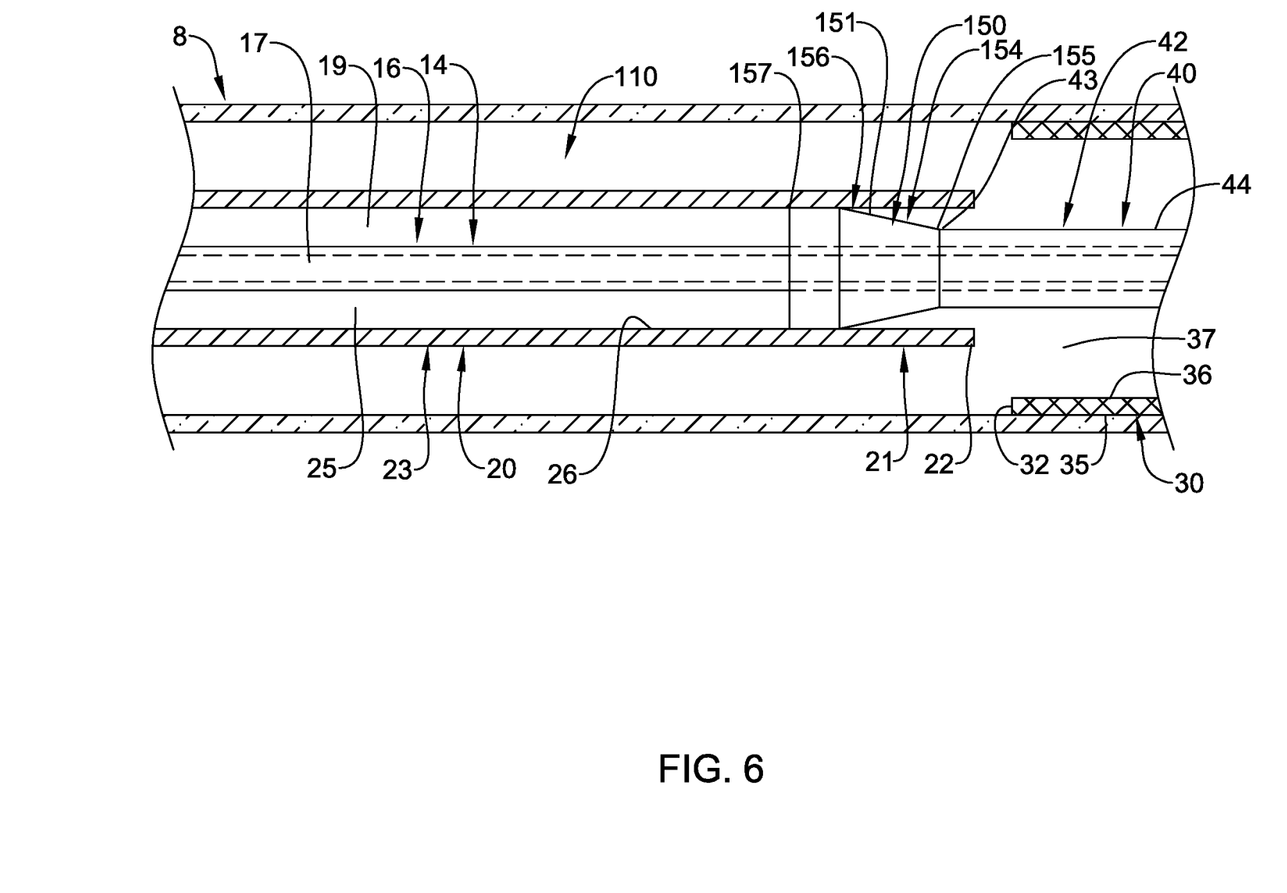
FIG. 6 is partial cross sectional side view of a portion of another example embodiment of a stent delivery system disposed within a vessel, shown in a configuration after deployment of the stent, and an anti-catch member is positioned within a deployment sheath spaced from and/or distal to the proximal end of the deployment sheath, wherein the vessel, stent, and deployment sheath are shown in cross-section side views, while an inner member and the intermediate member including the anti-catch member are shown in non-cross-sectional side view.
Figure 7:
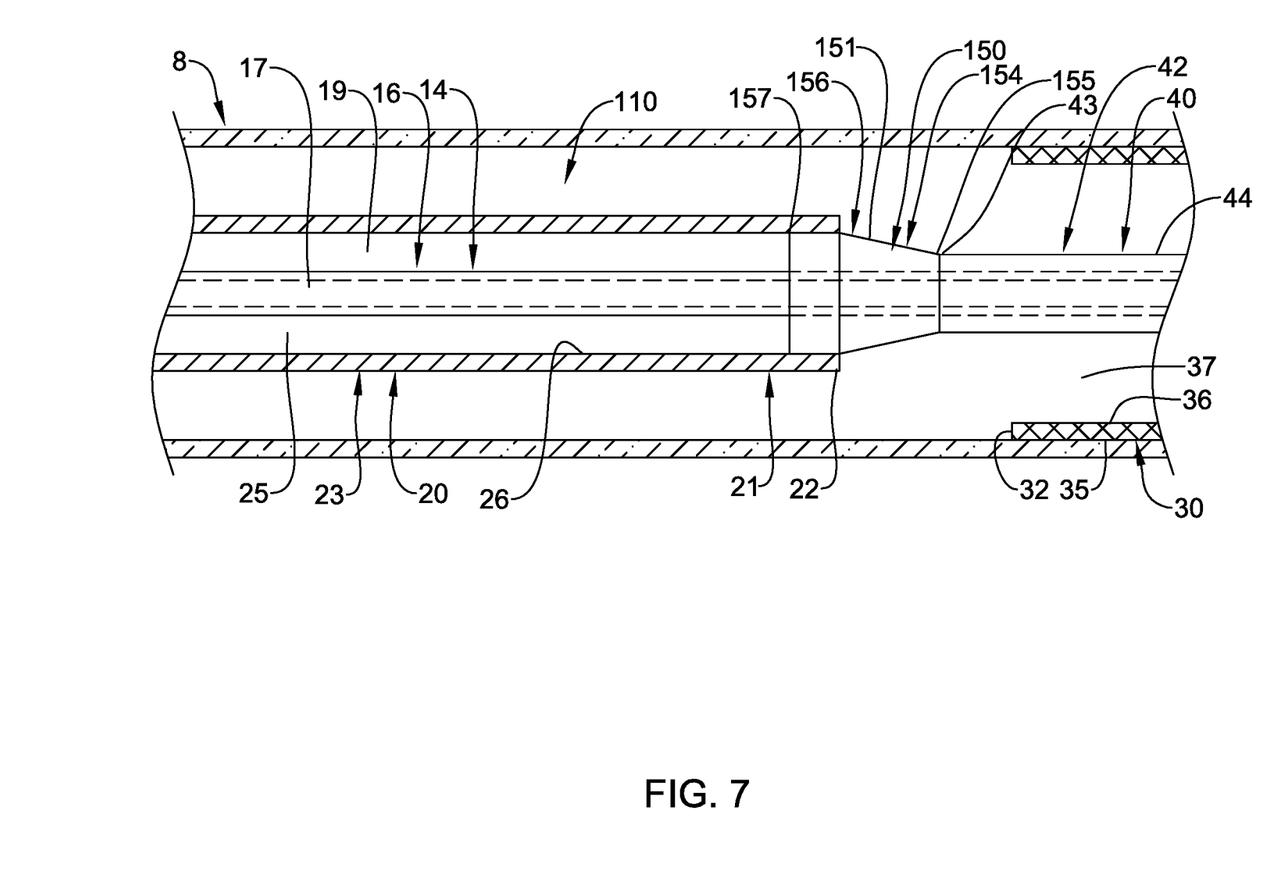
FIG. 7 is partial cross sectional side view of the example embodiment of FIG. 6, shown in another configuration where the intermediate member and anti-catch member are moved proximally relative to the deployment sheath such that the anti-catch member is positioned adjacent to the proximal end of the deployment sheath.

FIGS. 6 and 7 illustrate another example embodiment of a stent delivery system similar in form and function to stent delivery system shown and described with reference to FIGS. 1-5, wherein similarly named structures and/or similarly numbered structures may be similar in form, function and material as those discussed elsewhere herein. In this embodiment, however, the intermediate member 40 includes an anti-catch member 150 that is not collapsible/expandable. The anti-catch member 150 may be disposed on and/or along the distal end region 42 of the intermediate member 40, and may be coupled to the intermediate member 40 for movement therewith. The anti-catch member 150 may include a proximal region 154, a proximal end 155, a distal region 156, a distal end 157, and an outer surface 151. Some suitable but non-limiting materials for the anti-catch member 150 are, for example, metallic materials, polymer materials, composite materials, synthetic materials, etc., as are described below.

The anti-catch member 150 includes the tapered outer surface 151. For example, at least a portion of the anti-catch member 150 tapers from a smaller outer diameter to a larger outer diameter as it extends distally. Over at least a region of the length of the anti-catch member 150, an outer extent or diameter at a more distal portion of anti-catch member 150 is greater than an outer extent or diameter of the anti-catch member 150 at a more proximal portion thereof, and the transition between these different diameters may be tapered. As such, the anti-catch member 150 includes the distal portion 156 having a first outer diameter, and the proximal portion 154 having a second outer diameter, and the first outer diameter is greater than the second outer diameter. As can be appreciated, the anti-catch member 151 may be characterized as including a conically shaped tubular member. The taper may occur at a constant angle relative to the longitudinal axis, or may occur in a curvilinear fashion. In some embodiments, the taper may occur in a stepwise fashion, for example at varying angles along the length thereof.

As such, in some embodiments, the anti-catch member 150 may be a feature on and/or built onto the distal region of the intermediate member 40 that tapers to a thicker diameter as it extends distally. This thicker diameter and taper may help to mitigate the size and/or abruptness of the transition at the proximal end 22 of the deployment sheath 20, and may be designed to allow the proximal end 22 of the deployment sheath 20 to be passed through the stent 30 without catching on the stent.

The anti-catch member 150 may be a separate component affixed or attached to the intermediate member 40 using a suitable attachment technique, or may be part of and/or of monolithic or unitary construction with the intermediate member 40 (e.g. a singular part or component). For example, the anti-catch member 150 may be a separate tubular component that is bonded, welded, glued, soldered, heat shrunk or otherwise attached to the intermediate member 40. In other examples, the anti-catch member 150 may be an integral extension, portion, or part of the intermediate member 40 that includes a widened and/or increased diameter and/or tapered outer surface. In some embodiments, for example, as shown, the anti-catch member 150 is coupled to the distal end 43 of the intermediate member 40, and extends distally beyond the distal end 43 of the intermediate member 40, but other configurations are contemplated. For example, in other embodiments, the anti-catch member 150 may be disposed on and/or along the distal end region 42 of the intermediate member 40 such that it is spaced from (e.g. is proximal from) and/or overlaps the distal end 43 of the intermediate member 40.

FIG. 6 shows the stent deployment system 110 in a deployment configuration similar to that shown in FIG. 3, wherein the sent 30 has already been fully deployed. It is noted that the stent deployment system 110 as shown in FIG. 6 may have transitioned to the configuration shown from an initial and/or delivery configuration (similar to that shown in FIG. 1), where stent 30 would be in a compressed state disposed fully within the deployment sheath 20, through a partial deployment configuration (similar to that shown in FIG. 2), wherein the sent 30 is partially deployed. This transition would occur through the relative translation of the components as discussed herein. It is also noted that in these previous configurations (e.g. similar to FIGS. 1 and 2), the anti-catch member 150 would be disposed distally of the stent 30 within the deployment sheath 20, spaced from and/or distal to the proximal end 22 of the deployment sheath 20.

FIG. 6 then shows relative distal translation of the inner member 14 and the deployment sheath 20 relative to the stent 30 and the intermediate member 40 (including the anti-catch member 150). Or stated differently, FIG. 6 shows additional relative proximal translation of the stent 30 and intermediate member 40 (including the anti-catch member 150) relative to the inner member 14 and the deployment sheath 20. This additional relative translation of the components may release the intermediate and distal portions of the stent 30, progressively, from the deployment sheath 20, until the stent is fully deployed, as shown. During this translational movement, the anti-catch member 150 may again act as a distal stop and/or bumper for the stent 30, preventing distal movement of the stent 30 relative to and/or within the deployment sheath 20. The stent 30 exerts a radially outward force and expands once the deployment sheath 20 is removed therefrom. As such, the stent 30 is in a fully expanded configuration, and is deployed within the vessel. The distal region 42 of the intermediate member 40 is still disposed within the lumen of the stent 30. The deployment sheath 20 and the distal region of the 16 of the intermediate member 14 are disposed distally of the deployed stent 30. The anti-catch member 150 is disposed within the deployment sheath 20 (distal of the stent 30). In this configuration, the anti-catch member 150 has moved proximally within the deployment sheath 20 to a position which is closer to the proximal end 22, but is still in a position spaced from and/or distal of the proximal end 22.

FIG. 7 shows the stent deployment system 110 in another and/or withdrawal configuration, wherein the sent 30 is fully deployed, and the anti-catch member 150 has been moved to a position adjacent the proximal end 22 of the deployment sheath 20. In particular, FIG. 7 shows relative distal translation of the intermediate member 40, including the anti-catch member 150, relative to the inner member 14 and the deployment sheath 20. Or stated differently, FIG. 7 shows relative proximal translation of the inner member 14 and the deployment sheath 20 relative to the intermediate member 40, including the anti-catch member 150. This translation of the components may move the anti-catch member 150 to a position adjacent the proximal end 22 of the deployment sheath 20. In this embodiment, the anti-catch member 150 is not an expandable member, but provides a tapered transition adjacent the proximal end 22 of the deployment sheath 20. The distal region 42 of the intermediate member 40 is still disposed within the lumen of the deployed stent 30. The deployment sheath 20 and the distal region of the 16 of the intermediate member 14 are still disposed distally of the deployed stent 30. To withdraw the delivery system 10 from the anatomy, the deployment sheath 20 needs to be withdrawn proximally back through the deployed stent 30. The anti-catch member 150, when positioned adjacent to the proximal end 22 of the deployment sheath 20, may function to guard, cover, close, fill, reduce and/or protect all or a portion of the open proximal end 22 of the deployment sheath 20 and provide a tapered transition adjacent the open proximal end 22 of the deployment sheath 20 during withdrawal. As such, the deployment sheath 20 may be passed through the stent 30, and the anti-catch member 150 is designed to allow the proximal end 22 of the deployment sheath 20 to be passed through the stent 30 without catching on the stent.

As can be appreciate, any of the configurations of the stent deployment system 110 where the anti-catch member 150 is spaced from the proximal end 22 of the deployment sheath 20 may be considered a first position, and any of the configurations of the stent deployment system 10 where the anti-catch member 150 is adjacent the proximal end 22 of the deployment sheath 20 may be considered a second position, and that the anti-catch member 150 is movable relative to the deployment sheath 20 such that it can be transitioned from a first position to a second position.

The materials that can be used for the various components of the stent delivery systems (e.g. 10 and 110) disclosed herein may include those commonly associated with medical devices. For simplicity purposes, the following discussion makes reference to stent delivery systems (10 and 110). However, this is not intended to limit the devices and methods described herein, as the discussion may be applied to other similar stent delivery systems and/or components thereof.

The stent delivery systems 10 and 110 and/or other components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the stent delivery systems 10 and/or 110 and/or components thereof may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the stent delivery systems and/or other components thereof in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stent delivery systems and/or other components thereof to achieve the same result.

In some embodiments, a degree of Magnetic Resonance Imaging (MRI) compatibility is imparted into the stent delivery systems and/or other components thereof. For example, the stent delivery systems and/or other components thereof, or portions thereof, may be made of a material that does not substantially distort the image and create substantial artifacts (e.g., gaps in the image). Certain ferromagnetic materials, for example, may not be suitable because they may create artifacts in an MRI image. The stent delivery systems and/or other components thereof, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent delivery system, comprising:
an inner member having a distal end region;
a deployment sheath disposed along the distal end region of the inner member and defining a space between the inner member and the deployment sheath and configured to contain an entirety of a stent, the deployment sheath having a proximal end;
the inner member and the deployment sheath being designed to slide distally relative to the stent disposed in the space between the inner member and the deployment sheath in order to deploy the stent; and
an intermediate member disposed along the inner member and configured to extend within the stent when the stent is within the deployment sheath, the intermediate member including an anti-catch member, the intermediate member being movable relative to the deployment sheath such that the anti-catch member is positionable adjacent to the proximal end of the deployment sheath and designed to allow the proximal end of the deployment sheath to be passed through the stent without catching on the stent.

2. The stent delivery system of claim 1, wherein the anti-catch member includes a tapered outer surface.

3. The stent delivery system of claim 1, wherein the anti-catch member includes a collapsible member.

4. The stent delivery system of claim 1, wherein the anti-catch member includes a self-expanding member.

5. The stent delivery system of claim 1, wherein the anti-catch member includes a conically shaped tubular member.

6. The stent delivery system of claim 5, wherein the conically shaped tubular member includes a proximal portion coupled to the intermediate member, and an expandable distal portion.

7. The stent delivery system of claim 6, wherein the expandable distal portion includes a plurality of fingers.

8. The stent delivery system of claim 1, wherein the anti-catch member includes a distal portion having a first outer diameter, and a proximal portion having a second outer diameter, and the first outer diameter is greater than the second outer diameter.

9. The stent delivery system of claim 8, wherein the deployment sheath includes an inner diameter, and wherein the first outer diameter of the anti-catch member approaches the inner diameter of the deployment sheath.

10. The stent delivery system of claim 1, wherein the deployment sheath includes an inner surface, and the anti-catch member includes an outer surface that engages the inner surface of the deployment sheath.

11. The stent delivery system of claim 1, wherein the anti-catch member includes a tapered outer surface of a portion of the intermediate member.

12. The stent delivery system of claim 1, wherein the anti-catch member is movable relative to the deployment sheath such that it includes a first position in which the anti-catch member is spaced from the proximal end of the deployment sheath, and a second position in which the anti-catch member is positioned adjacent to the proximal end of the deployment sheath.

13. The stent delivery system of claim 1, wherein the anti-catch member is movable relative to the deployment sheath such that it includes a first position in which the anti-catch member is disposed within the deployment sheath distal of the proximal end of the deployment sheath, and a second position in which the anti-catch member is engaged with the deployment sheath at or adjacent the proximal end of the deployment sheath.

14. The stent delivery system of claim 1, wherein the anti-catch member includes a constrained configuration where the anti-catch member is disposed within the deployment sheath and an expanded configuration where at least a portion of the anti-catch member is disposed outside of the deployment sheath.

15. The stent delivery system of claim 1, wherein the anti-catch member includes an inner surface that is designed to engage an outer surface of the deployment sheath.

16. The stent delivery system of claim 1, further including a self-expanding stent disposed in the space between the inner member and the deployment sheath.

17. The stent delivery system of claim 16, where the anti-catch member is disposed in the space between the inner member and the deployment sheath.

18. A stent delivery system, comprising:
an inner member having a distal end region;
a deployment sheath coupled to the inner member and disposed along the distal end region of the inner member, the deployment sheath having a proximal end;
a stent disposed entirely within a space between the inner member and the deployment sheath;
an intermediate member disposed along the inner member within the stent and including an anti-catch member;
the inner member and the deployment sheath being designed to slide distally relative to the stent in order to deploy the stent; and
the intermediate member including the anti-catch member being movable relative to the deployment sheath such that the anti-catch member includes a first position in which the anti-catch member is spaced from the proximal end of the deployment sheath and a second position in which the anti-catch member is positioned adjacent to the proximal end of the deployment sheath and is designed to allow the proximal end of the deployment sheath to be passed through the stent without catching on the stent.

19. The stent delivery system of claim 18, wherein when in the first position, the anti-catch member is disposed within the space between the inner member and the deployment sheath, and when in the second position, at least a portion of the anti-catch member is disposed outside of the deployment sheath.

20. A method of deploying a stent, the method comprising:
delivering a stent delivery system into the anatomy of a patient, the stent delivery system including;
an inner member having a distal end region;
a deployment sheath disposed along the distal end region of the inner member, the deployment sheath having a proximal end;
a stent disposed entirely within a space between the inner member and the deployment sheath; and
an intermediate member disposed along the inner member within the stent and including an anti-catch member;
deploying the stent by sliding the inner member and the deployment sheath distally relative to the stent;
moving the anti-catch member relative to the deployment sheath such that the anti-catch member is positioned adjacent to the proximal end of the deployment sheath; and
passing the deployment sheath through the stent, wherein the anti-catch member is designed to allow the proximal end of the deployment sheath to be passed through the stent without catching on the stent.

\* \* \* \* \*